United States Patent [19]

Crooks

[11] 4,314,073
[45] Feb. 2, 1982

[54] PROCESS FOR THE PRODUCTION OF AN AROMATIC DICARBOXYLIC ACID

[75] Inventor: Graham R. Crooks, Guisborough, England

[73] Assignee: Imperial Chemical Industries Limited, London, England

[21] Appl. No.: 161,560

[22] Filed: Jun. 20, 1980

[30] Foreign Application Priority Data

Jul. 2, 1979 [GB] United Kingdom ............... 22989/79

[51] Int. Cl.³ ..................... C07C 51/56; C07C 51/42
[52] U.S. Cl. .................................. 562/416; 562/487; 562/494; 562/412; 562/417
[58] Field of Search ............... 562/487, 416, 417, 412, 562/494

[56] References Cited

U.S. PATENT DOCUMENTS 3,617,033  11/1971  Ichikawa et al. ................... 562/487
3,859,344   1/1975  Shigeyasu et al. .................. 562/414

FOREIGN PATENT DOCUMENTS 46-11170  3/1971  Japan ................................ 562/487
 983677   2/1965  United Kingdom .
1174953  12/1969  United Kingdom .
1350874   4/1974  United Kingdom .
1454478  11/1976  United Kingdom .
2003862   3/1979  United Kingdom .

Primary Examiner—Alan Siegel
Attorney, Agent, or Firm—Cushman, Darby & Cushman

[57] ABSTRACT

A substituted aromatic compound e.g. p-xylene is oxidized to an aromatic dicarboxylic acid e.g. terephthalic acid using a Co/Mn/Br catalyst in acetic acid and the slurry product is purified by treating with molecular oxygen and diluting with fresh acetic acid before separation of the terephthalic acid and mother liquor.

10 Claims, No Drawings

PROCESS FOR THE PRODUCTION OF AN AROMATIC DICARBOXYLIC ACID

The present invention relates to a process for the manufacture of an aromatic dicarboxylic acid eg terephthalic acid.

Aromatic dicarboxylic acids are widely used as polymer intermediates by virtue of their two acid-functional groups. Terephthalic acid in particular is of outstanding importance in the polymer field and is the starting material for the production of a range of polyesters in particular polyethyleneglycolterephthalate. For this purpose the terephthalic acid must be pure otherwise a coloured or defective polymer tends to be produced.

The most commonly used method for the manufacture of terephthalic acid is by the oxidation of p-xylene the reaction conventionally being carried out in acetic acid as solvent using a catalyst comprising a cobalt compound, a manganese compound and a bromine compound. The oxidation of the p-xylene proceeds through a number of intermediates i.e. p-xylene→p-tolualdehyde→p-toluic acid→p-carboxybenzaldehyde (4-CBA)→terephthalic acid and at the end of the reaction the terephthalic acid is obtained as a slurry in acetic acid. The major, and most serious, impurity in the terephthalic acid in the slurry is 4-CBA which may be present in an amount of 2000 to 3000 ppm and which tends to give rise to discoloured polyester.

Various methods have been used to reduce the 4-CBA content of the terephthalic acid, the most common involving the catalytic hydrogenation of the terephthalic acid to hydrogenate and remove the 4-CBA. This purification step is however expensive and more recently processes have been developed which by choice of catalyst and oxidation reaction conditions enable purer terephthalic acid to be produced in the oxidation stage e.g. terephthalic acid contained about 1000 ppm 4-CBA.

Terephthalic acid which contains about 1000 ppm 4-CBA is almost suitable for polymer manufacture and for this reason processes which produce such a product have been in some instances called "single-stage" processes. There have however been attempts to reduce further the 4-CBA content of the single-stage product by using a "secondary" oxidation stage in which the crude slurry from the first or primary oxidation is submitted to further contact with oxygen in a separate stage. By this means the 4-CBA content of the terephthalic acid is further reduced.

A slurry of terephthalic acid in acetic acid is the crude product of the single-stage process whether the latter has one or two oxidation stages. It is advantageous to filter this slurry hot under pressure and then to wash the solid so obtained with fresh acetic acid thereby reducing still further its 4-CBA content. The filtration of the slurry on a commercial scale is however a very expensive step because of the cost of the pressure filter required which must be fabricated in very expensive corrosion resistant material.

In British Patent Application Ser. No 2,000,493 we have described a single-stage process in which at the end of the oxidation the necessity of a filtration step is avoided by allowing the terephthalic acid crystals to separate under gravity in a washing zone in which they fall into fresh acetic acid fed to the bottom of the zone the displaced mother liquor being removed from an upper region of the washing zone.

We have now found that a significant reduction in the 4-CBA content of the terephthalic acid may be made by a process in which the mother liquor of the oxidation product slurry is diluted with, rather than displaced by, acetic acid, while at the same time continuing to contact the slurry with oxygen so reducing the capital cost of the equipment required. This process is particularly applicable to the production of terephthalic acid but may also be used in the production of other aromatic carboxylic acids.

According to the invention therefore a process for the production of an aromatic carboxylic acid comprises oxidising, with molecular oxygen in a primary oxidation stage, an aromatic compound substituted by at least one alkyl, hydroxyalkyl or formyl group in a solvent in the presence of a heavy metal oxidation catalyst to produce a slurry of said aromatic carboxylic acid in said solvent and adding fresh solvent and molecular oxygen to said slurry after the primary oxidation stage but before the separation of the aromatic carboxylic acid from the slurry mother liquor.

The process preferably includes a secondary oxidation stage after the primary oxidation stage and the fresh solvent may be added in this stage or subsequent thereto.

The aromatic compounds to be oxidised by the process of our invention are substituted by alkyl, hydroxyalkyl or formyl groups. Particularly suitable alkyl groups are methyl, ethyl and isopropyl groups; particularly suitable hydroxyalkyl groups are hydroxymethyl and hydroxyethyl groups. One, two or more such groups may be present in the aromatic nucleus and the groups may be the same or different. The aromatic nucleus may, for example, be a benzene or naphthalene nucleus. Particularly suitable aromatic compounds to be oxidised are toluene, ethylbenzene, isopropylbenzene, o-, m- and p-xylene, cumene, pseudocumene, the isomeric diisopropylbenzenes, durene, mesitylene, hydroxymethylbenzene, hydroxyethylbenzene, bis-hydroxymethylbenzenes, benzaldehyde, the isomeric tolualdehydes and 2,6-dimethyl-naphthalene. Suitable aromatic compounds also include those which are already partially oxidised to carboxylic acids and their corresponding esters, for example p-toluic acid, methyl p-toluate and p-carboxybenzaldehyde. The process of our invention is particularly suitable for the oxidation of p-xylene to terephthalic acid.

The solvent used in the process of our invention is a solvent for the aromatic compound to be oxidised. The solvent should be substantially unaffected under the oxidation conditions. Particularly suitable solvents are carboxylic acids, especially lower aliphatic monocarboxylic acids having from 2 to 8 carbon atoms and benzoic acid. Acetic acid is a preferred solvent. Water may also be used as a solvent.

The heavy metals used as catalysts include vanadium, chromium, manganese, iron, cobalt, nickel, molybdenum, cerium and zirconium. Particularly suitable is cobalt especially in combination with manganese and possibly also with cerium or zirconium. The heavy metals are used, for example, in the form of their inorganic or organic acid salts especially the bromides or acetates. The catalyst may be used in conjunction with an oxidation promoter, for example an aldehyde or ketone such as acetaldehyde or methyl ethyl ketone, or especially, a source of bromine e.g. a bromide. Suitable bromides are, for example, bromides of the heavy metals used, for example cobalt or manganese bromides, alkali metal or ammonium bromides or hydrobromic acid. Bromine itself, or organic bromo compounds such as tetrabromoethane may also be used as the source of bromine.

The oxygen used in the primary oxidation stage may be pure oxygen or may be a mixture of oxygen with an inert gas e.g. nitrogen. Conveniently the oxygen is provided in the form of air.

The primary oxidation may be carried out at temperatures in the range 80° to 270° C. preferably 160° to 230° C. When the heavy metal catalyst is a mixture of cobalt and manganese the mixture may contain a preponderance of cobalt, e.g. 800 to 5000 ppm preferably 1200 to 2500 ppm of the solvent of cobalt and 1 to 30 wt % manganese preferably 1 to 20 wt % manganese based on the cobalt. Alternatively the proportion of manganese may be increased and the cobalt may, for example, comprise 100 to 700 ppm solvent and the manganese 0.5 to 1.5 times the weight of cobalt. The "high" cobalt process is preferably carried out at a temperature in the range 160° to 190° C. preferably 160° to 180° C. and the "high manganese" process at 205° to 225° C. Whichever process is adopted it is preferred that a bromine promoter is present at a level in the range 400 to 20000 ppm based on the solvent. In the "high cobalt" process it is preferred that the bromine is at least 1.5 times the combined weight of cobalt plus manganese more preferably 1.5 to 5 times the combined weight while for the "high manganese" process it is preferred that the bromine be 400 to 2000 ppm by weight based on the solvent.

Water is formed in the oxidation of the aromatic compound and although it is beneficial, for reasons of catalyst solubility, to have some water present, when an organic solvent is used too much water is detrimental to the oxidation. Preferably therefore the water content in the solvent in the primary oxidation stage is 1 to 10% more preferably 1 to 7% by weight.

The weight ratio of aromatic compound e.g. p-xylene to solvent e.g. acetic acid in the primary oxidation stage is preferably 4:1 to 7:1 more preferably 4:1 to 6:1 and the reaction time 0.5 to 2 hours. The pressure should be at least such that a liquid phase is maintained in the reactor and may be, for example in the range 1 to 50 bar, preferably 10 to 50 bar.

The secondary oxidation stage may be carried out under similar conditions to the primary oxidation except that it is preferred that the oxidation temperature be less than the temperature of the primary oxidation suitably less than T°C. but greater than T-50° C. where T is the primary oxidation temperature. The secondary oxidation may be carried out using oxygen or a mixture of oxygen with an inert gas. Preferably the oxidising gas is air or contains less oxygen than does air and in the latter case the exhaust gas from the primary oxidation stage may be used.

The secondary oxidation stage may be fed continuously or intermittently with reaction slurry from the primary oxidation stage the residence time of slurry in the secondary oxidation preferably being 0.1 to 2 hours. According to one aspect of the invention fresh solvent may be added at this stage during the secondary oxidation process. Alternatively, if fresh solvent is not added at the secondary oxidation stage, it may be added together with molecular oxygen to the oxidation reaction product slurry in a separate "reslurry" stage of the process after the secondary oxidation has been completed. The weight of fresh solvent added to the slurry is suitably 0.1 to 10 times, preferably 0.5 to 5 times and more preferably 4 to 5 times the weight of the aromatic carboxylic acid in the slurry. Too little fresh solvent results in a less pure aromatic carboxylic acid product while too much fresh solvent has the effect of increasing the cost of the process because a larger vessel is required to obtain the same residence time of slurry in contact with the fresh solvent. The fresh solvent is conveniently added to the secondary oxidation or reslurry stage in a similar manner to the addition of slurry from the primary oxidation e.g. if slurry is continuously transferred from the primary oxidation to the secondary oxidation and continuously withdrawn from the latter then the fresh solvent may also be continuously added. The temperature of the fresh solvent which is added to the secondary oxidation or reslurry stage is preferably the same as the temperature of the slurry in this oxidation or reslurry stage. If the fresh solvent is added in a reslurry stage then the molecular oxygen which is also added may be in a form similar to that used in the secondary oxidation i.e. preferably in a gas containing less oxygen than does air e.g. an exhaust gas from an earlier oxidation stage.

Following the addition of fresh solvent the slurry of aromatic carboxylic acid in solvent passes in turn to a series of crystallisers interspersed by centrifuges in which the slurry is cooled and filtered and the solid aromatic acid washed and filtered once again. Generally two such crystallisers and two centrifuges are sufficient, cooling of the slurry with accompanying pressure reduction taking place in each crystalliser.

In its preferred form the process includes a secondary oxidation stage and the fresh solvent is added at this stage rather than to a reslurry stage after the secondary oxidation. In this way the capital cost of plant equipment is reduced by eliminating the need for a reslurry vessel.

The invention will now be further described with reference to the following Examples in which the apparatus used was as follows:

The reactor had a capacity of 4 liters and was fabricated from titanium. The reactor was provided with means for the continuous introduction of a feed solution by means of a pump from a reservoir, a gas inlet and means for the withdrawal of a vapour stream and the slurry product of the oxidation. The vapours were condensed and returned to the reactor as reflux after removal of part of their water content. The slurry removal means was connected to a second 4 liter titanium reactor provided with a gas inlet and with means for adding fresh solvent and for withdrawing product slurry which in turn was fed to a 2 liter cooler/crystalliser.

The gas fed to the first, or primary oxidation, reactor comprised 550 liters/hour nitrogen, and 150 liters/hour oxygen. The feed solution hourly rate comprised 180 grams p-xylene, 8 grams catalyst (2250 ppm cobalt as cobalt acetate tetrahydrate, 100 ppm manganese as manganese acetate tetrahydrate and 4000 ppm bromine as a 47% w/w hydrogen bromide solution in water) 200 grams water and 2200 grams acetic acid. The amount of water in the acetic acid returned as reflux was such as to maintain a water concentration of 5% w/w in the reactor. The temperature in the reactor was 170°-175° C. and the pressure 7.2 bar. The temperature in the second reactor or secondary oxidation vessel was 160° C. and the gas fed was 250 liters/hour of 8% v/v oxygen in nitrogen. The gas leaving the primary and secondary reactors contained respectively 4% v/v oxygen and 7.5% v/v oxygen. The third vessel was held at 75° C. and 2 bar pressure in which cooling took place by flash evaporation of acetic acid.

The effectiveness of the process was measured by determining the 4-CBA content of the terephthalic acid produced by the oxidation. In the results reported in the following Table each oxidation was divided into two parts, in the first part the reactions were run under steady conditions for six hours and the 4-CBA figure reported is the value achieved over the last three of the six hours. After six hours conditions were changed as shown and the experiment continued for a further six hours the 4-CBA figure recorded being that achieved under steady conditions in the last three hours of the second six hour period. In the Table therefore 0–6 hours refers to the conditions in the secondary oxidiser in that period and similarly 6–12 hours the conditions in the secondary oxidiser in the second half of the experiment. "Time" indicates the mean residence time of slurry in the secondary oxidiser.

| | 0–6 hrs | | | 6–12 hrs | | | |
|---|---|---|---|---|---|---|---|
| EXAMPLE | gas | Fresh acetic liter/hr | 4-CBA ppm | gas | Fresh acetic liter/hr | 4-CBA ppm | Time (mins) |
| 1 | 8% $O_2$ | — | 420 | $N_2$ | — | 570 | 75 |
| 2 | 8% $O_2$ | — | 465 | 8% $O_2$ | 1.5 | 435 | 33 |
| 3 | $N_2$ | — | 598 | 8% $O_2$ | 1.5 | 420 | 33 |
| 4 | $N_2$ | — | 620 | $N_2$ | 1.5 | 585 | 31 |
| 5 | 8% $O_2$ | 1.5 | 430 | $N_2$ | 1.5 | 550 | 32 |

Example 1 shows the improvement achieved by secondary oxidation alone (150 ppm reduction in 4-CBA).

Example 2 shows the effect of adding fresh acetic acid to the secondary oxidation (30 ppm reduction in 4-CBA).

Example 3 shows the combined effects of secondary oxidation and addition of fresh solvent (178 ppm reduction in 4-CBA).

Example 4 shows the effect of addition of fresh acetic acid with no secondary oxidation (35 ppm reduction in 4-CBA).

Example 5 shows the effect of secondary oxidation when fresh acetic acid is added (120 ppm reduction in 4-CBA).

A second series of experiments were carried out in which the mean residence time of slurry in the secondary reactor was increased. Otherwise the conditions and method of operation were the same as described in Examples 1 to 5. The results were as follows:

| | | 0–8 hrs | | |
|---|---|---|---|---|
| EXAMPLE | gas | Fresh Acetic Acid liters/hr | 4-CBA ppm | Time (mins) |
| 6 | 8% $O_2$ | — | 455 | 134 |
| 7 | 8% $O_2$ | — | 460 | 75 |
| 8 | 8% $O_2$ | 1.0 | 370 | 69 |
| 9 | 8% $O_2$ | 1.2 | 320 | 65 |
| 10 | 8% $O_2$ | 1.2 | 300 | 59 |

Examples 6 and 7 show that no extra benefit is obtained by increasing the residence time over 75 minutes. Examples 8, 9 and 10 show the combined benefits of secondary oxidation and addition of fresh solvent.

In a further series of experiments the slurry from the secondary reactor was split into two parts. One part (a) was filtered hot through a pressure filter and the resulting solid was extracted with fresh acetic acid at 160° C. for 2 hours using an acetic acid:terephthalic acid ratio of 3:1. The other part (b) of the slurry was simply mixed with fresh acetic acid in a ratio of 3 parts acetic acid to 1 part terephthalic acid and a mixture of 8% oxygen in nitrogen passed into the slurry. The quality of the terephthalic acid obtained by the two methods was compared.

The results are given below:

| EXAMPLE | 4-CBA content before treatment | 4-CBA content (a) | 4-CBA content after treatment (b) |
|---|---|---|---|
| 11 | 530 | 440 | 380 |
| 12 | 960 | 440 | 400 |
| 13 | 470 | 440 | 390 |

The conditions present in Examples 6 to 10 were repeated except that in each of Examples 14 and 15 one factor was changed. The results were as follows:

| EXAMPLE | 4-CBA content before treatment | 4-CBA content (a) | 4-CBA content (b) |
|---|---|---|---|
| 14 | 390 | 280 | 320 |
| 15 | 872 | 435 | 520 |

In Example 14(a) the slurry was diluted with 3 pts acetic acid to 1 part terephthalic acid in the slurry and 8% oxygen in nitrogen was passed through the slurry.

In example 14(b) the oxygen was omitted the gas consisting of nitrogen alone leading to an increase in the final 4-CBA content.

In Example 15(a) the slurry was treated as in Example 14(a) while in 15(b) the slurry was diluted with 2 parts of acetic acid to 1 part terephthalic acid in the slurry. Examples 16 to 23

In these Examples the extent of the oxidation of the acetic acid solvent was measured as well as the purity of the terephthalic acid produced. The oxidation of the acetic acid in the primary oxidiser was determined by measuring the oxides of carbon evolved, the results being expressed as moles of carbon oxides per mole p-xylene. Results for a range of p-xylene to solvent ratios in the primary oxidation and fresh acetic acid to terephthalic acid ratios in the slurry in the secondary oxidation are given in the following Table.

| Example | Solvent ratio wt acetic acid:wt p-xylene in the primary oxidation | Grams Fresh acetic acid :grams terephthalic acid in the slurry | Carbon Oxides | 4-CBA content of the terephthalic acid |
|---|---|---|---|---|
| 16 | 3:1 | 2.82:1 | 0.29 | 550 ppm |
| 17 | 3:1 | 3.39:1 | 0.29 | 480 ppm |
| 18 | 3:1 | 4.22:1 | 0.29 | 410 ppm |
| 19 | 4:1 | 3.52:1 | 0.32 | 390 ppm |
| 20 | 4:1 | 4.22:1 | 0.32 | 405 ppm |

-continued

| Example | Solvent ratio wt acetic acid:wt p-xylene in the primary oxidation | Grams Fresh acetic acid :grams terephthalic acid in the slurry | Carbon Oxides | 4-CBA content of the terephthalic acid |
| --- | --- | --- | --- | --- |
| 21 | 4.5:1 | 4.60:1 | 0.33 | 300 ppm |
| 22 | 5:1 | 4.22:1 | 0.35 | 300 ppm |
| 23 | 6:1 | 4.92:1 | 0.47 | 260 ppm |

I claim:

1. In a process for the production of an aromatic carboxylic acid which comprises oxidising with molecular oxygen in a primary oxidation stage an aromatic compound substituted by at least one alkyl, hydroxyalkyl or formyl group in a solvent in the presence of a heavy metal oxidation catalyst optionally in conjunction with an oxidation promoter to produce a slurry of said aromatic carboxylic acid in said solvent the improvement in which fresh solvent and molecular oxygen are added to said slurry after the primary oxidation stage but before the separation of the aromatic carboxylic acid from the slurry mother liquor.

2. A process according to claim 1 in which the process comprises a secondary oxidation stage after the primary oxidation stage and the fresh solvent is added at this stage or the fresh solvent and molecular oxygen are added after the secondary oxidation stage in a reslurry stage.

3. A process according to claim 2 in which the fresh solvent is added at the secondary oxidation stage and the temperature of this stage is less than T° C. but greater than T-50° C. where T is the primary oxidation temperature.

4. A process according to claim 2 in which the fresh solvent is added at the secondary oxidation stage and the oxidising gas used in this stage contains less oxygen than does air.

5. A process according to claim 4 in which the oxidising gas for the secondary oxidation is the exhaust gas from the primary oxidation stage.

6. A process according to claim 2 in which the fresh solvent is added at the secondary oxidation stage and the residence time of slurry in this stage is 0.1 to 2 hours.

7. A process according to claim 1 in which the weight of fresh solvent added to the slurry is 0.1 to 10 times the weight of aromatic carboxylic acid in the slurry.

8. A process according to claim 1 in which the temperature of fresh solvent which is added is the same as the temperature of the slurry.

9. A process according to claim 2 in which terephthalic is produced by oxidising an aromatic compound selected from the group consisting of p-xylene, p-tolualdehyde, p-toluic acid and p-carboxybenzaldehyde in the presence of a heavy metal oxidation catalyst comprising cobalt and manganese and a source of bromine as oxidation promoter in acetic acid solvent at a temperature in the range 80° C. to 270° C. and at a weight ratio of aromatic compound to acetic acid in the primary oxidation of 4:1 to 7:1.

10. A process according to claim 9 in which the weight ratio of aromatic compound to acetic acid in the primary oxidation is 4:1 to 6:1 and the weight of fresh solvent added to the slurry is 4 to 5 times the weight of terephthalic acid in the slurry.

* * * * *